(12) United States Patent
Berberian et al.

(10) Patent No.: US 11,915,831 B2
(45) Date of Patent: *Feb. 27, 2024

(54) LEARNING FILTER FOR THE DETECTION OF INDICATORS IN HEALTHCARE DATA

(71) Applicant: Laboratory Corporation of America Holdings, Burlington, NC (US)

(72) Inventors: Lance Berberian, Burlington, NC (US); Prashant Gupta, Chapel Hill, NC (US); Jessie Lunk, Durham, NC (US)

(73) Assignee: Laboratory Corporation of America Holdings, Burlington, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/053,881

(22) Filed: Nov. 9, 2022

(65) Prior Publication Data

US 2023/0071721 A1  Mar. 9, 2023

Related U.S. Application Data

(63) Continuation of application No. 16/260,959, filed on Jan. 29, 2019, now Pat. No. 11,532,398.

(Continued)

(51) Int. Cl.
*G16H 50/30* (2018.01)
*G16H 50/50* (2018.01)
(Continued)

(52) U.S. Cl.
CPC ............ *G16H 50/30* (2018.01); *G16H 10/20* (2018.01); *G16H 10/40* (2018.01); *G16H 10/60* (2018.01);
(Continued)

(58) Field of Classification Search
CPC ........ G16H 50/30; G16H 10/20; G16H 10/40; G16H 10/60; G16H 10/65; G16H 50/20; G16H 50/50; G16H 50/70; G16H 80/00
See application file for complete search history.

(56) References Cited

U.S. PATENT DOCUMENTS 10,446,273 B1 * 10/2019 McNair .................. G16H 10/60
11,532,398 B2    12/2022 Berberian et al.
(Continued)

FOREIGN PATENT DOCUMENTS

WO       2016162767 A1    10/2016

OTHER PUBLICATIONS

A framework for administrative claim data to explore healthcare coordination and collaboration Uddin, Shahadat, PhD; Kelaher, Margaret, PhD; Srinivasan, Uma, PhD. Australian Health Review 40.5: 500-510. Collingwood: CSIRO. (2016) (Year: 2016).*

(Continued)

*Primary Examiner* — Amber A Misiaszek
(74) *Attorney, Agent, or Firm* — Kilpatrick Townsend & Stockton LLP

(57) ABSTRACT

A system includes a learning filter for deidentified healthcare data. The system provides self-improving data filtering of data for the detection of disorders for engaging patients in observational research to gather additional data. A processor performs operations including obtaining patient information about a patient and current order data. The current order data indicates an order for a laboratory test for the patient and obtaining, from a database, historical data indicating a previous laboratory test for the patient and a result of the previous laboratory test. The operations further include determining that the patient is a subject of interest for a disorder by applying the filter to historical data to produce filtered data and comparing the filtered data to a profile (Continued)

associated with the disorder. Additional laboratory tests can be performed, after which a hash-to-patient identifier (PID) mapping database and the filter can be updated.

17 Claims, 5 Drawing Sheets

Related U.S. Application Data

(60) Provisional application No. 62/623,361, filed on Jan. 29, 2018.

(51) Int. Cl.
*G16H 10/60* (2018.01)
*G16H 10/20* (2018.01)
*G16H 10/40* (2018.01)
*G16H 50/70* (2018.01)
*G16H 50/20* (2018.01)
*G16H 10/65* (2018.01)
*G16H 80/00* (2018.01)

(52) U.S. Cl.
CPC ............. *G16H 10/65* (2018.01); *G16H 50/20* (2018.01); *G16H 50/50* (2018.01); *G16H 50/70* (2018.01); *G16H 80/00* (2018.01)

(56) References Cited

U.S. PATENT DOCUMENTS

| | | | | |
|---|---|---|---|---|
| 2001/0037023 | A1* | 11/2001 | Chen | C07D 401/14 544/335 |
| 2003/0187615 | A1* | 10/2003 | Epler | G16H 40/20 702/181 |
| 2007/0294110 | A1* | 12/2007 | Settimi | G16H 10/60 705/3 |
| 2012/0060216 | A1* | 3/2012 | Chaudhri | G06Q 10/10 726/21 |
| 2013/0124523 | A1* | 5/2013 | Rogers | G16H 10/60 707/741 |
| 2015/0106123 | A1* | 4/2015 | Amarasingham | G06Q 50/01 705/3 |
| 2015/0193583 | A1* | 7/2015 | McNair | G16H 50/20 705/2 |

OTHER PUBLICATIONS

U.S. Appl. No. 16/260,959 , "Advisory Action", dated Dec. 30, 2022, 4 pages.
U.S. Appl. No. 16/260,959 , "Final Office Action", dated May 25, 2022, 18 pages.
U.S. Appl. No. 16/260,959 , "Final Office Action", dated Oct. 14, 2023, 25 pages.
U.S. Appl. No. 16/260,959 , "Non-Final Office Action", dated Feb. 3, 2022, 15 pages.
U.S. Appl. No. 16/260,959 , "Non-Final Office Action", dated Apr. 15, 2021,U. 19 pages.
U.S. Appl. No. 16/260,959 , "Notice of Allowance", dated Aug. 17, 2022, 15 pages.
CA Patent Appication No. CA 3,088,136 , "Office Action", dated Feb. 15, 2023 , 11 pages.
CA Patent Application No. CA 3,088,136 , "Office Action", dated August 3, 202 , 5 pages.
CA Patent Application No. CA 3 ,088,136 , "Office Action", dated Apr. 25, 2022, 6 pages.
IN Patent Application No. IN202037036624 , "First Examination Report", dated Apr. 28, 2022, 5 pages.
U.S. PCT Application No. PCT/US2019/015615 , "International Preliminary Report on Patentability", dated Aug. 13, 2020, 9 pages.
U.S. PCT Application No. PCT/US2019/015615 , "International Search Report and Written Opinion", dated Apr. 25, 2019, 12 pages.

\* cited by examiner

LEARNING FILTER FOR THE DETECTION OF INDICATORS IN HEALTHCARE DATA

CROSS-REFERENCE TO RELATED APPLICATIONS

The present application is a continuation of and claims priority from commonly owned U.S. patent application Ser. No. 16/260,959, entitled, "Learning Filter for Detection of Indicators in Healthcare Data," filed Jan. 29, 2019, which claims priority from provisional patent application 62/623,361, filed Jan. 29, 2018. The entire disclosure of each of these applications is incorporated herein by reference.

FIELD

The present application generally relates to healthcare information and more specifically relates automated, self-improving data filtering in a system using stored de-identified data for the detection of data that may indicate disorders. The detection may be used for engaging patients in observational research to gather additional data.

BACKGROUND

Observational research can include determining whether a patient is a subject of interest for a particular disorder. However, some such disorders of interest are difficult to diagnose, which can prevent a patient that is a subject of interest from being discovered. Moreover, medical data for such patients is typically stored in a highly secure and complex fashion, which may include deidentifying the data and relying on hash tables, encryption and other data security techniques that restrict use to parties authorized through appropriate digital credentials to identify data and match the data with the patient.

SUMMARY

Various examples of systems and methods using a data filter to find data for use in the detection of rare disorders are disclosed herein. In one example, a system includes a processing device and a non-transitory computer-readable medium communicatively coupled to the processing device. The non-transitory computer-readable medium includes computer program code executable by the processing device to cause the processing device to perform operations. The operations include obtaining patient information about a patient and current order data, wherein the current order data indicates an order for a laboratory test for the patient and obtaining, from a database, historical data indicating a previous laboratory test for the patient and a result of the previous laboratory test. The operations further include determining that the patient is a subject of interest for a disorder by applying a filter to the historical data to produce filtered data and comparing the filtered data to a profile associated with the disorder. The operations further include determining a first additional laboratory test for updating the profile associated with the disorder, the filter, or both, the profile and the filter usable for determining whether the patient likely has the disorder. The operations further include storing deidentified data including the patient information, current order data, historical data, first additional laboratory test, and a result, with the deidentified data being stored in a secure registry database. The operations further include updating a hash-to-patient identifier (PID) mapping database to enable identifying the deidentified data and updating the filter, the profile, or both.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

DETAILED DESCRIPTION

Examples are described herein in the context of systems and methods of disorder detection. The following description is illustrative only and is not intended to be in any way limiting. Reference will now be made in detail to implementations of examples as illustrated in the accompanying drawings. The same reference indicators will be used throughout the drawings and the following description to refer to the same or like items.

Systems and methods described herein allow for the development and refinement of detecting stored data that may indicate a disorder in a patient. In one example, when one or more laboratory tests is ordered for a patient, a determination is made based on stored data as to whether the patient is a subject of interest for a disorder. A learning filter is applied to the data, and filtered data is compared to a profile. Specimen(s) for the one or more laboratory tests and one or more add-on tests specified as a result of the determination are collected from the patient the tests are performed. If the information including one or more add-on tests, laboratory and medical history of the patient, and patient following over time (e.g., monitoring the patient over time), suggest medical action or indicates that the patient has or likely has the disorder, then a notification is provided to the patient and the patient's physician. The composite information including the results from the one or more add-on tests and information gathered from following patients over time can be used to revise the criteria for analyzing data to determine future subjects of interests for the disorder by automatically training the learning filter. In this way, the accuracy of the determination of relevant subjects of interest for the disorder can be continually improved as data on additional patients is gathered.

Illustrative Systems

Figure 1:
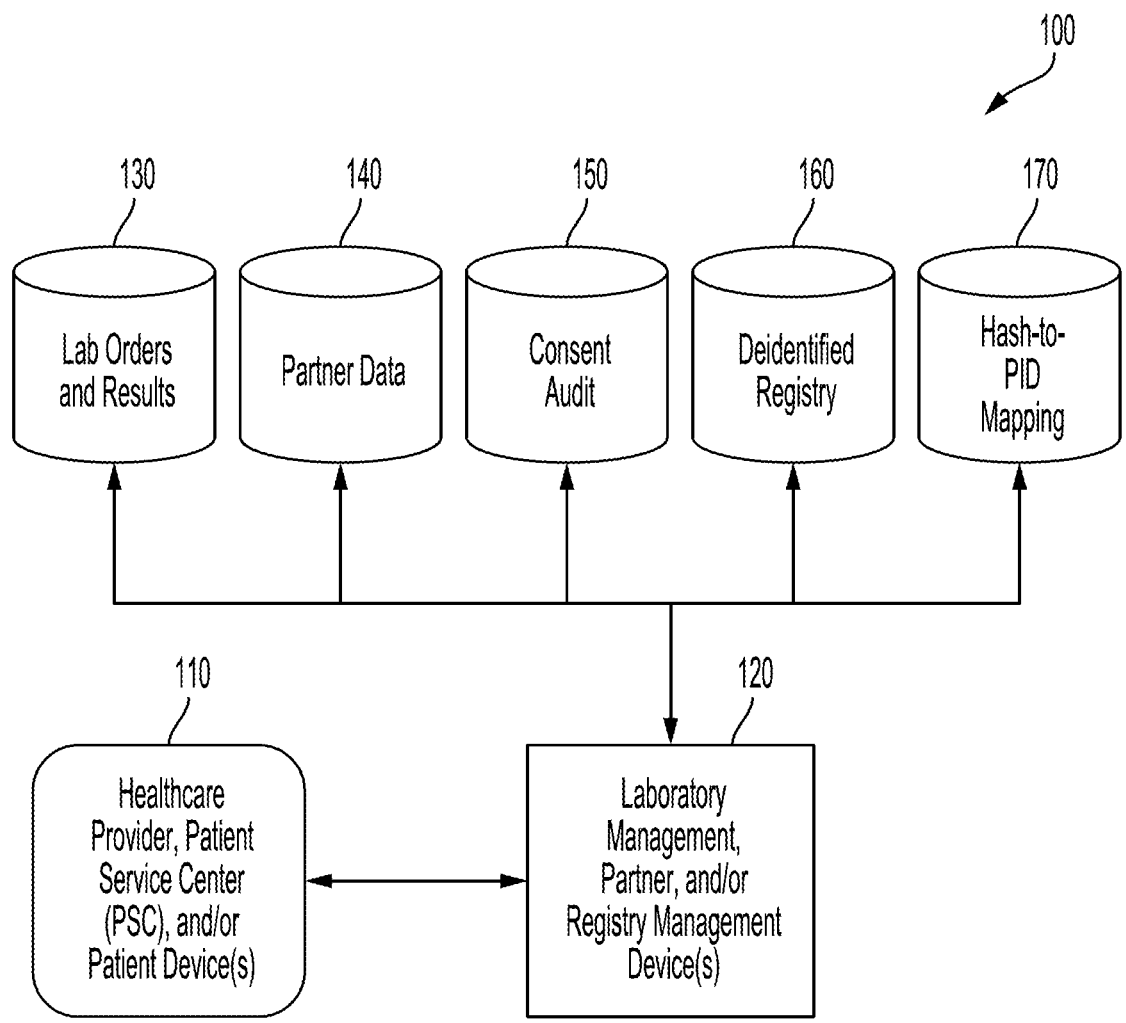
FIG. 1 shows a system for the detection of data indicating disorders according to an example.

Referring now to FIG. 1, this figure shows an example system 100 for disorder detection. System 100 includes one or more healthcare provider, patient service center (PSC), and/or patient devices 110 in communication with one or more laboratory management, partner, and/or registry management device(s) 120. In system 100, the one or more laboratory management, partner and/or registry management device(s) 120 are in communication with multiple databases (e.g., 130, 140, 150, 160, 170). The databases may include one or more laboratory orders and results databases 130, one or more partner data databases 140, one or more consent audit databases 150, one or more deidentified registry databases 160, and/or one or more hash-to-patient identifier (PID) mapping databases 170. As discussed in more detail below, system 100 can be used to implement a process analyzing data to detect indications of a disorder detection, such as process 300 shown in FIG. 3 or process 400 shown in FIG. 4.

One or more of the healthcare provider, PSC, and/or patient devices 110 can be a smartphone, tablet, laptop, desktop, or other suitable computing devices. One or more of devices 110 can be used to order laboratory tests for patients. For example, a physician, nurse practitioner, registered nurse, and/or other healthcare personnel may use one or more of devices 110 to order one or more laboratory tests for a patient.

One or more of devices 110 can be used to receive patient information. For example, a patient, patient service center personnel, physician, nurse practitioner, registered nurse, and/or other healthcare personnel may use one or more of devices 110 to input the patient's name, address, phone number, email, medications, medical conditions, and/or other patient information.

One or more of devices 110 can be used in processing laboratory tests for patients. For example, a PSC personnel, physician, nurse practitioner, registered nurse, and/or other healthcare personnel may use one or more of devices 110 to input specimen information for one or more specimens received from a patient to complete one or more laboratory tests ordered for the patient. As another example, one or more of devices 110 may be used to input specimen information for one or more specimens received from a patient to complete one or more add-on laboratory tests that may indicate whether the patient has a particular disorder.

One or more of devices 110 can be used to enroll patients in laboratory test results reporting or to receive laboratory test results for completed laboratory tests. For example, a patient, PSC personnel, physician, nurse practitioner, registered nurse, and/or other healthcare personnel may use one or more of devices 110 to enroll patients in a laboratory test results reporting service that allows the patient to access the results of completed laboratory tests through laboratory test results reporting website. In this example, after a patient is enrolled in the laboratory test results reporting service, the patient can access the laboratory test results reporting website to access the results of the patient's completed laboratory tests using the patient's device(s).

One or more of devices 110 can be used to provide inputs indicating that patients are interested in and/or consent to participating in one or more rare disease registries or studies. For example, a patient, patient service center personnel, physician, nurse practitioner, registered nurse, or other healthcare personnel may use one or more of devices 110 to input that the patient is interested in and consents to participating in a disease study for which the patient has been determined to be a subject of interest. In some examples, a patient, patient service center personnel, physician, nurse practitioner, registered nurse, and/or other healthcare personnel may use one or more of devices 110 to input that the patient consents to providing medical information about the patient.

One or more of devices 110 can be used to provide inputs for patient surveys. For example, a patient, patient service center personnel, physician, nurse practitioner, registered nurse, and/or other healthcare personnel may use one or more of devices 110 to provide inputs to complete a patient survey corresponding to a disease study for which the patient has been determined to be a subject of interest.

One or more devices 110 can be used to receive notifications regarding enrolled patients. For example, if a determination is made that a patient has a disorder or likely has a disorder, then a notification can be received by one or more of devices 110 to alert the patient of his or her disorder. As another example, if a determination is made that a patient with a disorder is eligible for a particular clinical trial, then a notification can be received by one or more of devices 110 to alert the patient to the clinical trial.

One or more laboratory management, partner, and/or registry management device(s) 120 can be a server or another suitable computing device. One or more of devices 120 can receive laboratory orders for patients received from devices 110. For example, one or more of devices 120 can receive an order for a laboratory test for a patient from one or more of devices 110 and store the order in the laboratory orders and results database 130. The order for the laboratory test can include additional information such as, for example, metadata associated with the order for the laboratory test. Examples of metadata can include a diagnosis code associated with the laboratory order and/or result, a specialty of a physician, nurse practitioner, registered nurse, or other healthcare personnel associated with the laboratory order, a location of a physician, nurse practitioner, registered nurse, and/or other healthcare personnel associated with the laboratory order, a date associated with the laboratory order (e.g., a date, time, etc.).

One or more of devices 120 can be used in processing laboratory orders. For example, one or more of devices 120 can store the results of a laboratory test for a patient in the laboratory orders and results database 130. One or more of devices 120 can access historical laboratory results for patients. For example, one or more of devices 120 can access the results of prior laboratory tests for a patient stored in the laboratory orders and results database 130. While laboratory orders and results are in the same database 130 in the example in FIG. 1, in some examples laboratory orders and results may be in separate databases. For example, laboratory orders may be in one database and laboratory results may be in a different database.

One or more of devices 120 can access partner data. For example, one or more of devices 120 may access partner data 140 when an order for a laboratory test for a patient is received to determine whether the patient qualifies as a subject of interest for one or more disorder studies. The lab orders and results database 130 may also be accessed to obtain the laboratory test(s) that was ordered for the patient or historical medical data for the patient which can also be used in determining whether the patient qualifies as a subject of interest for one or more disorder studies.

One or more of devices 120 may access patient consent data. For example, one or more of devices 120 can access consent data in consent audit database 150 to determine whether a patient has consented to participating in one or more disorder registries or studies or determine whether the patient has consented to provide medical information about the patient.

One or more of devices 120 may access one or more deidentified registries 160, one or more hash-to-patient identifier (PID) mapping databases 170, or both. For example, one or more of devices 120 can deidentify patient information or laboratory test results and store the deidentified data in deidentified registry 160. In this example, one or more of devices 120 can store one or more mappings in hash-to-PID mapping database 170 such that the deidentified data in deidentified registry 160 can be identified. For example, one or more of devices 120 may read deidentified data in deidentified registry 160 and read mappings in hash-to-PID mapping database 170 to identify the patients and laboratory test results for the patients.

Figure 2:
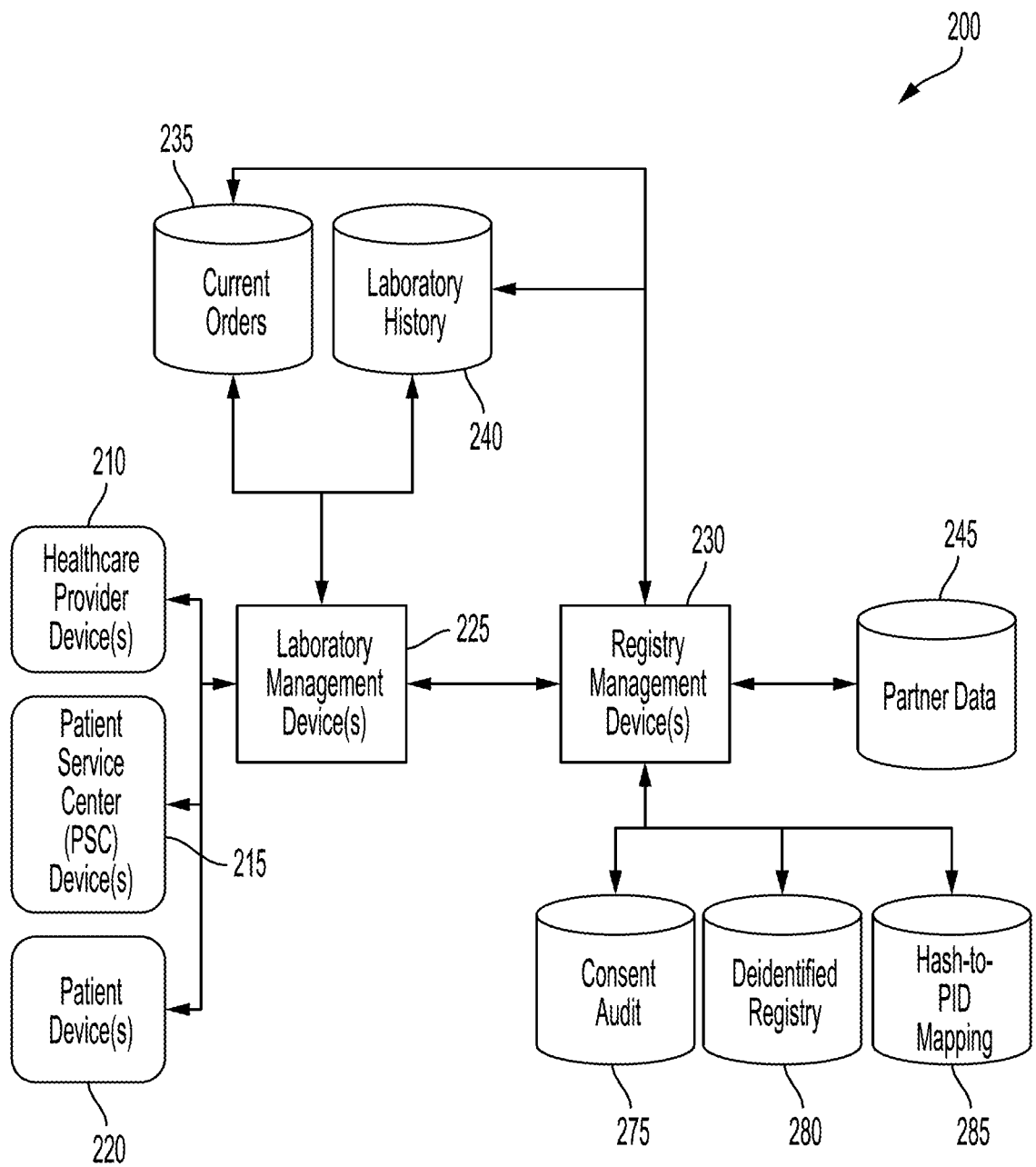
FIG. 2 shows a system for the detection of data indicating disorders according to an example.

Referring now to FIG. 2, this figure shows an example system 200 for detecting data that is indicative of a disorder. System 200 includes one or more healthcare provider devices 210, one or more patient service center (PSC) devices 215, one or more patient devices 220, one or more laboratory management (LM) device(s) 225, one or more registry management (RM) devices 230, and multiple databases (e.g., 235, 240, 245, 275, 280, 285). As discussed in more detail below, system 200 can be used to implement a process of data detection, such as process 300 shown in FIG. 3 or process 400 shown in FIG. 4.

In system 200, the healthcare provider device(s) 210, PSC device(s) 215, and patient device(s) 220 are in communication with LM device(s) 225. The healthcare provider device(s) 210 can be one or more smartphones, tablets, laptops, desktops, other suitable computing devices, or a combination thereof. The healthcare provider device(s) 210 may be one or more devices used by a physician, nurse practitioner, registered nurse, other personnel of a healthcare provider, or a combination thereof. For example, healthcare provider device(s) 210 may be used to order one or more laboratory tests for patients. LM device(s) 225 can receive laboratory orders from the healthcare provider device(s) 210.

The PSC device(s) 215 can be one or more smartphones, tablets, laptops, desktops, other suitable computing devices, or a combination thereof. The PSC device(s) 215 may be one or more devices used by personnel of a patient service center. For example, PSC device(s) 215 may be used to input the patient's name, address, phone number, email, medications, medical conditions, and/or other patient information. As another example, PSC device(s) 215 may be used to input specimen information for one or more specimens received from a patient to complete one or more laboratory tests ordered for the patient. As another example, PSC device(s) 215 may be used to input specimen information for one or more specimens received from a patient to complete one or more add-on laboratory tests that may indicate whether the patient has a particular disorder.

The patient device(s) 220 can be one or more smartphones, tablets, laptops, desktops, other suitable computing devices, or a combination thereof. The patient device(s) 220 may be one or more devices used by a patient for which a laboratory test is ordered. For example, patient device(s) 220 can be used to enroll patients in laboratory test results reporting and/or to receive laboratory test results for completed laboratory tests. In some examples, healthcare provider device(s) 210 may be used to enroll patients in laboratory test results reporting and/or to receive laboratory test results for completed laboratory tests. In some examples, PSC device(s) 215 may be used to enroll patients in laboratory test results reporting.

Patient device(s) 220 may be used by patients to provide input stating that the patient is interested in and/or consents to participating in a disease study for which the patient has been determined to be a subject of interest. Patient device(s) 220 may be used by patients to provide inputs to complete a patient survey corresponding to a study for which the patient has been determined to be a subject of interest.

Patient device(s) 220 can receive notifications to alert patients that they have or may have a disorder. For example, if a determination is made based on the results of a laboratory test, the patient's laboratory test history, the patient's medical history, or monitoring the patient that a patient has or likely has a disorder, then a patient device 220 corresponding to the patient can receive a notification to alert the patient that he or she has or likely has the disorder. As another example, if a determination is made that a patient with a disorder is eligible for a particular clinical trial, then a patient device 220 corresponding to the patient can receive a notification to alert the patient that he or she is eligible for that clinical trial.

In system 200, the LM device(s) 225 is in communication with registry management (RM) device(s) 230. The LM device(s) 225 is also in communication with multiple databases. These databases can include a current orders database 235 and/or a laboratory history database 240. The current orders database 235 can include information such as patient data (e.g., patient name, address, insurance, etc.), healthcare provider data (e.g., healthcare provider name, specialty, etc.), laboratory tests currently ordered for patients, a result of the laboratory tests currently ordered for the patients, data about a context surrounding the laboratory tests currently ordered for the patients, a timing of the laboratory tests currently ordered for the patients (e.g., time, date, etc.). The laboratory history database 240 can include information from laboratory tests that have been completed. For example, laboratory history database 240 may include information such as laboratory tests previously ordered for patients, add-on tests for patients, and results of laboratory tests for patients. Moreover, while current laboratory orders are shown in database 235 and laboratory histories are shown in database 240 in the example in FIG. 2, in some examples current laboratory orders and laboratory histories may be in a single database or in additional databases.

LM device(s) 225 can be a server and/or another suitable computing device. LM device(s) 225 can receive laboratory orders for patients received from healthcare provider device(s) 210. For example, LM device(s) 225 can receive an order for a laboratory test for a patient from a healthcare provider device 210 and store the order in the current orders database 235.

LM device(s) 225 can be used in processing laboratory orders. For example, LM device(s) 225 can store the results of a laboratory test for a patient in the laboratory history database 240. LM device(s) 225 can access historical laboratory results for patients. For example, LM device(s) 225 can access the results of prior laboratory tests for a patient stored in the laboratory history database 240. While current laboratory orders and laboratory history are stored in current orders database 235 and laboratory history database 240, respectively, in the example in FIG. 2, in some examples laboratory orders and laboratory history may be store in the same database or additional databases.

In system 200, the RM device(s) 230 is in communication with the LM device(s) 225, and multiple databases. These databases may include current orders database 235, laboratory history database 240, partner data database 235, consent audit database 275, deidentified registry 280, and/or hash-to-PID mapping database 285. In some examples, partner data database 235, consent audit database 275, deidentified registry 280, and/or hash-to-PID mapping database 285 may be the same or similar databases as the partner data database 140, consent audit database 150, deidentified registry 160, and/or hash-to-PID mapping database 170, respectfully, described herein with respect to FIG. 1.

RM device(s) 230 can be a server and/or another suitable computing device. RM device(s) 230 may access current order data stored in the current orders database 235 and/or laboratory history data stored in laboratory history database 240. In some examples, RM device(s) 230 access such data by directly accessing current orders database 235 and/or laboratory history database 240. In some examples, RM device(s) 230 access such data by one or more intermediary devices, such as LM device(s) 225.

RM device(s) 230 may access partner data. For example, RM device(s) 230 may access partner data database 245 when an order for a laboratory test for a patient is received by LM device(s) 225 and LM device(s) 225 contacts RM device(s) 230. In this example, RM device(s) may access partner data database 245 in determining whether the patient qualifies as a subject of interest for one or more disorder studies. The current orders database 235 and/or laboratory history database 240 may also be accessed by RM device(s) 230 to obtain the laboratory test(s) that was ordered for the patient and/or historical medical data for the patient which can also be used in determining whether the patient qualifies as a subject of interest for one or more disorder studies.

RM device(s) 230 may access patient consent data. For example, RM device(s) 230 can access consent data in consent audit database 275 to determine whether a patient has consented to participating in one or more disorder registries or studies or to determine whether the patient has consented to providing medical information about the patient.

RM device(s) 230 may access deidentified registry 280 and/or hash-to-patient identifier (PID) mapping database 285. For example, LM device(s) 225 and/or RM device(s) 230 can deidentify patient information and/or laboratory test results and store the deidentified data in deidentified registry 280. In some examples, LM device(s) 225 and/or RM device(s) 230 can store one or more mappings in hash-to-PID mapping database 285 such that the deidentified data in deidentified registry 280 can be identified. For example, LM device(s) 225 and/or RM device(s) 230 may read deidentified data in deidentified registry 280 and read mappings in hash-to-PID mapping database 285 to identify the patients and laboratory test results for the patients.

Illustrative Methods of Disorder Detection

Figure 3:
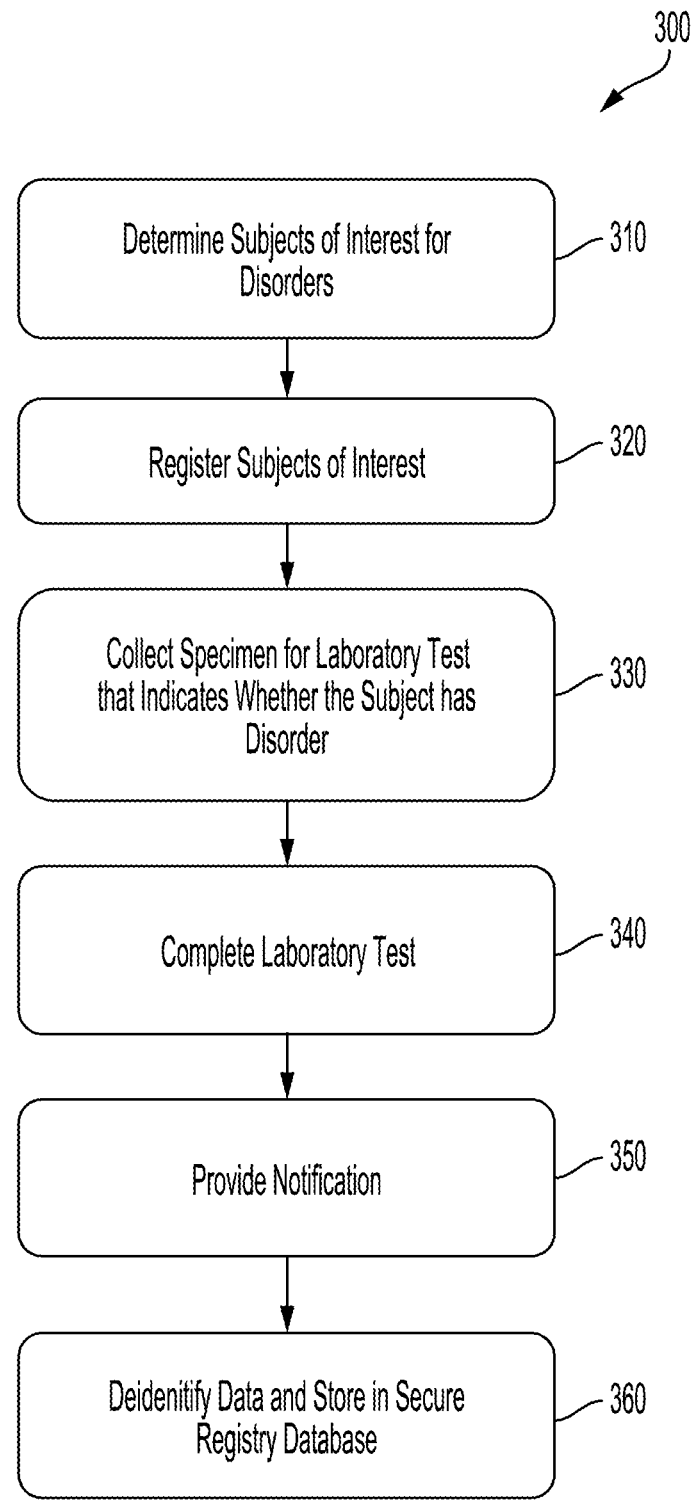
FIG. 3 shows a process of data detection according to an example.

Referring now to FIG. 3, this figure shows an example of a process 300 of disorder detection. Reference will be made with respect to system 200 shown in FIG. 2; however, system 100 shown in FIG. 1 or any other suitable system may be employed according to various examples.

Process 300 begins in block 310 when one or more subjects of interest for a disorder is determined. In one example, a patient enters a patient service center (PSC) for specimen collection for an existing laboratory testing order. A patient identification for the patient—such as the patient's name, address, phone number, patient number, laboratory order number, etc.—is input into PSC device(s) 215 and sent from PSC device(s) 215 to LM device(s) 225. In some examples, LM device(s) 225 send the patient identification to RM device(s) 230. Based on the patient identification, current order data stored in current orders database 235 and historical laboratory orders or results for the historical laboratory orders stored in laboratory history database 240, are analyzed to determine whether the patient satisfies criteria to be a subject of interest for a disorder. In some examples, partner data (such as insurance claims, electronic health records, pharmacy data) corresponding to the patient and stored in partner data database 245 may also be used to determine whether the patient satisfies criteria to be a subject of interest for a disorder.

In block 320, one or more subjects of interest is registered. For example, if a patient in a PSC for specimen collection for an existing laboratory testing order is determined to be a subject of interest for a disorder, then the patient can be asked whether he or she would like to register in a disorder registry. In this example, LM device(s) 225 and/or RM device(s) may send a registration invite to the patient via PSC device(s) 215 and/or patient device(s) 220. The registration invite can involve the patient agreeing to have extra specimen drawn, confirming his or her primary physician, providing consent to contact the patient's primary physician with medically relevant results, and/or consent to be contacted with medically relevant results.

In block 330, one or more specimens for one or more laboratory tests that indicate whether a subject has a disorder or likely has the disorder is collected. For example, if a patient is determined to be a subject of interest for a disorder and the patient registers to be included in the disorder registry, then one or more add-on specimen(s) required to complete add-on laboratory test(s) that indicate whether the patient has or likely has a disorder is determined. In this example, while the patient is at the PSC, these add-on specimens are collected from the patient in addition to any specimens required to complete the previously-ordered laboratory tests for the patient. Information corresponding to the add-on specimen for the add-on laboratory tests may be input into PSC device(s) 215 and sent to LM device(s) 225 and/or RM device(s) 230.

In block 340, the one or more laboratory tests are completed. For example, the previously-ordered laboratory tests can be completed. The add-on laboratory tests that indicate whether the patient has the disorder can be completed. In some examples, the add-on laboratory tests can be used to complete or update a laboratory profile for the disorder that indicates whether a patient likely has the disorder. Results for the laboratory tests can be stored in a database. In some examples, results for the laboratory test can include metadata about the laboratory test such as, for example, data about a specialty of a physician, nurse practitioner, registered nurse, and/or other healthcare personnel associated with the laboratory test, a location of a physician, nurse practitioner, registered nurse, and/or other healthcare personnel associated with the laboratory test, a date associated with the laboratory test (e.g., a date, time, etc.), a diagnosis code associated with the laboratory test. For example, referring to FIG. 2, LM device(s) 225 or registry management device(s) 230 may store results of the add-on laboratory tests in laboratory history database 240.

In block 350, one or more notifications may be provided. For example, if results for the add-on laboratory tests specify medically actionable results (e.g., the results for the add-on laboratory tests indicate that the patient has or likely has the disorder or indicate that the patient needs additional laboratory testing to determine whether the patient has or likely has the disorder), then a notification may be provided to the patient's primary physician, the patient, or both. In some examples, a notification is provided by RM device(s) 230 or LM device(s) 225 to a healthcare provider device 210 of the patient's primary physician. In some examples, a notification is proved by RM device(s) 230 or LM device(s) 225 to a patient device 220 of the patient.

In block 360, data is deidentified and stored in a secure registry database. For example, referring to FIG. 2, patient data can be deidentified and stored in deidentified registry 280. In this example, hash-to-PID mappings, which can be used to identify the patient data stored in deidentified registry 280, can be stored in hash-to-PID mapping database 285. In one example, when the add-on laboratory test(s) is completed, the patient's data can be deidentified and integrated into deidentified registry database 280. Information stored in deidentified registry may be used for further investigational use. Registered patients may continue to be tracked following the completion of the add-on laboratory tests to follow the progression of treatments, symptoms, laboratory results, and/or natural disorder history.

Figure 4:
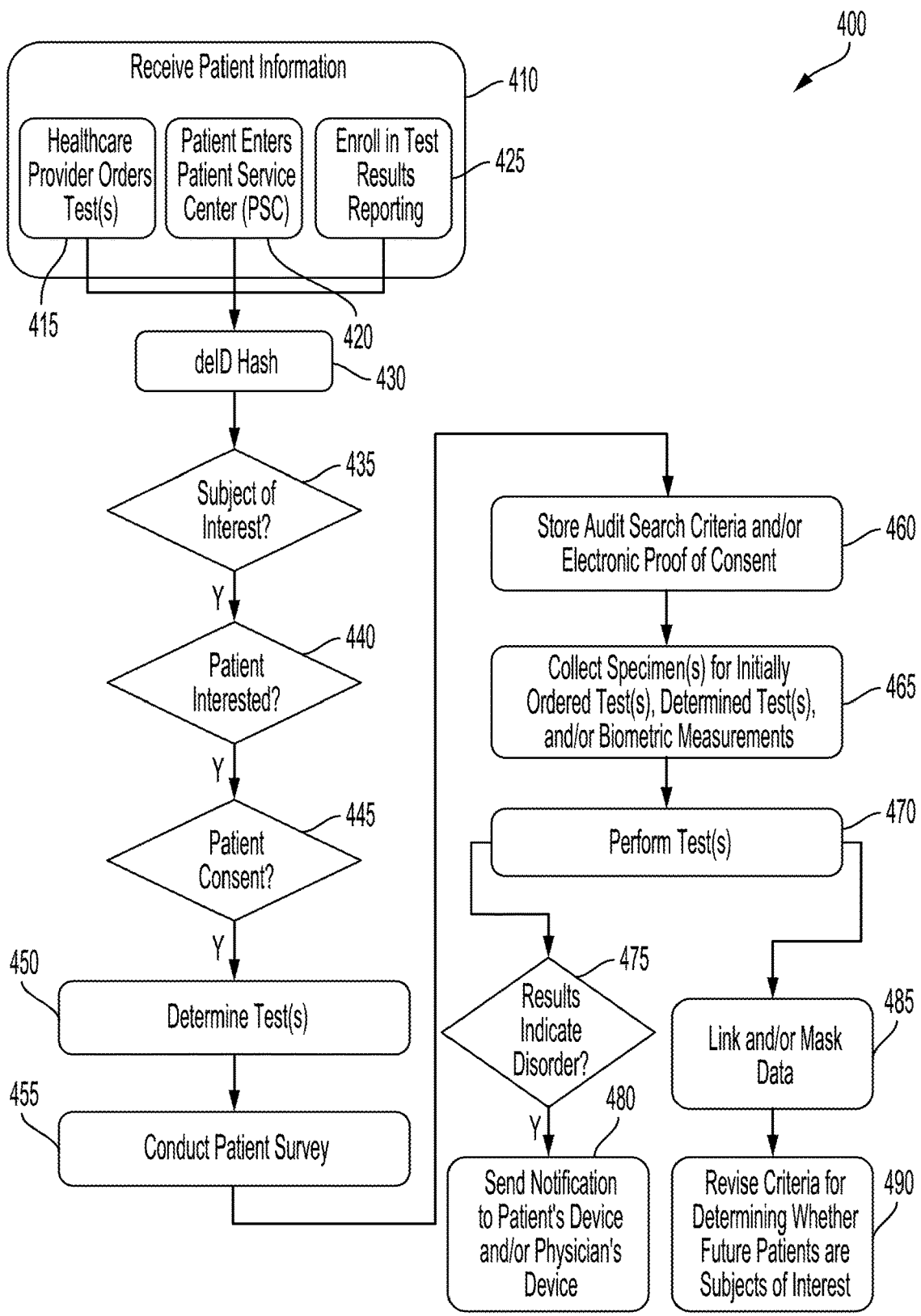
FIG. 4 shows a process of data detection according to an example.

Referring now to FIG. 4, this figure shows an example of a process 400 of disorder detection. Process 400 may be implemented using system 100 shown in FIG. 1, system 200 shown in FIG. 2, or any other suitable system according to various examples. Process 400 begins in block 410 when patient information is received. For example, referring to FIG. 1, one or more of devices 120 may receive patient information from one or more of devices 110. As another example, referring to FIG. 2, LM device(s) 225 may receive patient information from healthcare provider device(s) 210, PSC device(s) 215, and/or patient device(s) 220.

As shown in block 415, patient information can be received when a healthcare provider orders one or more tests for a patient. For example, referring to FIG. 2, patient information may be received by LM device(s) 225 when an order for one or more laboratory tests for a patient is ordered using one or more of the healthcare provider device(s) 210. In some examples, the laboratory tests can be ordered for a patient using a healthcare provider device 210 and the ordered laboratory tests are received by LM device(s) 225.

As shown in block 420, patient information can be received when a patient visits a patient service center (PSC) to have one or more specimens collected for one or more previously ordered laboratory tests. For example, referring to FIG. 2, patient information may be received by LM device(s) 225 when a patient visits a PSC to have one or more specimens collected for one or more previously ordered laboratory tests and the patient information is input using PSC device(s) 215.

As shown in block 425, patient information can be received when a patient enrolls in a test results reporting service. For example, referring to FIG. 2, patient information may be received by LM device(s) 225 as part of a patient enrolling in test results reporting using patient device(s) 220.

In block 430, a deidentified hash is generated. For example, LM device(s) 225 and/or RM device(s) 230 may generate a deidentified hash. In block 435, a determination is made as to whether the patient is a subject of interest for a disorder. For example, RM device(s) 230 may determine whether the patient is a subject of interest for one or more disorders. In some examples, unique criteria for each of multiple disorders is used to evaluate whether the patient is a subject of interest for any of the disorders. In another example, a laboratory profile for the disorder can be used to evaluate whether the patient is a subject of interest for any of the disorders. The patient's currently ordered laboratory tests, laboratory order test history, laboratory order test results history, and/or partner data may be accessed and used in determining whether a patient is a subject of interest for a particular disorder. RM device(s) 230 may access data corresponding to the patient stored in current orders database 235, laboratory history database 240, and/or partner data database 245 in determining whether a patient is a subject of interest for a particular disorder.

In block 440, if a determination is made that the patient is a subject of interest for a possible disorder, then a determination is made as to whether the patient is interested in enrolling in a study. For example, RM device(s) 230 may send an enrollment interest request to a patient device 220 corresponding to the patient. As examples, the enrollment interest request may be sent to a patient via short message service (SMS), email, or through a website to a patient device 220 corresponding to the patient.

In block 445, if a determination is made that the patient is interested in enrolling in the study, then a determination is made as to whether the patient has consented to enrolling in the study. For example, if the patient provides a response to the enrollment interest request using the patient device 220 corresponding to the patient that he or she is interested in enrolling in a study, then RM device(s) 230 may determine whether the patient has consented to enrolling in the study. The patient's response to the enrollment interest request may be sent from the patient device 220 corresponding to the patient to the RM device(s) 230 via SMS, email, through the website, via an application or software on the patient device 220, or via any other suitable method.

Once the RM device(s) 230 has received a response to the enrollment interest request indicating that the patient is interested in enrolling in the study, RM device(s) 230 can determine whether the patient has consented to enrolling in the study. For example, RM device(s) 230 can access consent audit database 275 to determine whether the patient has consented to enrolling in the study. If the patient has not already consented, then RM device(s) 230 can send consent information to the patient device 220 corresponding to the patient. The RM device(s) 230 may receive the patient's consent to enroll in the study from the patient device 220 corresponding to the patient.

In block 450, one or more tests for the patient is determined. The test(s) may be designed to indicate whether a patient has the disorder for which the patient is a subject of interest as determined in block 235. In another example, the test(s) may be designed to update or complete a laboratory profile for the disorder that indicates a likelihood of a patient having the disorder.

In block 455, a patient survey is conducted. For example, referring to FIG. 2, RM device(s) 230 outputs the survey to a patient device 220 corresponding to the patient. In this example, the patient can complete the survey using the patient device 220 corresponding to the patient. The completed survey can be sent from the patient device 220 corresponding to the patient to the RM device(s) 230.

In block 460, audit search criteria or electronic proof of consent is stored. For example, referring to FIG. 2, if the patient has not already provided consent in block 445 and thus provides consent, then an electronic proof of consent received by RM device(s) 230 from patient device 220 corresponding to the patient may be stored in consent audit database 275 by RM device(s) 230.

In block 465, one or more specimens are collected for the initially ordered laboratory test(s) (such as described herein with respect to block 415) and/or the determined add-on laboratory test(s) (such as described herein with respect to block 450). In some examples, biometric measurements for the patient may also be collected. After the specimen(s) have been collected, in block 470 the initially ordered tests or the determined test(s) are performed using the collected specimen(s).

After the results for the determined add-on laboratory test(s) have been generated, in block 475 a determination is made as to whether the results indicate the disorder for which the patient is a subject of interest. As another example, after the results for the determined add-on laboratory test(s) have been generated, in block 475 a determination is made as to whether the results indicate that the patient likely has the disorder for which the patient is a subject of interest. For example, RM device(s) 230 and/or LM device(s) 225 may analyze the patient's results of the add-on laboratory tests and various (e.g., normal) ranges of results of the add-on laboratory tests to determine whether the patient's results are outside of the various ranges of results in determining whether the results indicate that the patient has the disorder or likely has the disorder. In some examples, the various ranges of results can be based on results from laboratory tests on one or more other patients or individuals. For example, the RM device(s) 230 and/or LM device(s) 225 compares the patient's results of the add-on laboratory tests to the various or normal ranges of results of the add-on laboratory tests and determines that the results indicate that the patient has the disorder or likely has the disorder if the results are outside of the various or normal ranges. As another example, the RM device(s) 230 and/or LM device(s) 225 compares the patient's results of the add-on laboratory tests to the various or normal ranges of results of the add-on laboratory tests and determines that the results do not indicate that the patient has the disorder or that the patient likely does not have the disorder if the results are within the various or normal ranges. In some examples, the patient's results of the add-on laboratory tests may indicate that other laboratory test(s) need to be performed in order to determine whether the patient has the disorder or likely has the disorder.

If a determination is made that the results indicates that the patient has or likely has the disorder or needs additional testing, in block 480 a notification is sent to the patient's device and/or the patient's physician's device. For example, referring to FIG. 2, RM device(s) 230 may send a notification to a healthcare provider device 210 corresponding to the patient's physician stating that the patient has or likely has the disorder or that additional testing is required to determine whether the patient has or likely has the disorder. As another example, RM device(s) 230 may send a notification to a patient device 220 corresponding to the patient stating that the patient has or likely has the disorder or that additional testing is required to determine whether the patient has or likely has the disorder. Examples of how a notification may be sent include SMS, email, through a website, via an application or software on the RM device 230, or via any other suitable method.

After the results for the determined add-on laboratory test(s) have been generated, in block 485 data is linked and may be masked. In one example, the results for the determined add-on laboratory test(s) can be masked and stored in deidentified registry 280 by RM device(s) 230 and/or LM device(s) 225. In some examples, information can be unmasked from deidentified registry 280 using hash-to-PID mapping database 285.

In block 490, criteria for determining whether future patients are subjects of interests for the disorder is revised. For example, referring to FIG. 2, data stored in deidentified registry 280 may be used to improve the criteria for when a patient is considered a subject of interest for a particular disorder. As another example, a laboratory profile for the disorder that indicates whether a patient likely has the disorder is revised or updated. In some examples, the laboratory profile for the disorder can include one or more tests that are designed to indicate whether a patient has the disorder for which the patient is a subject of interest as determined in block 235. In this way, the criteria for determining subjects of interest for disorders can be refined and improved over time.

Figure 5:
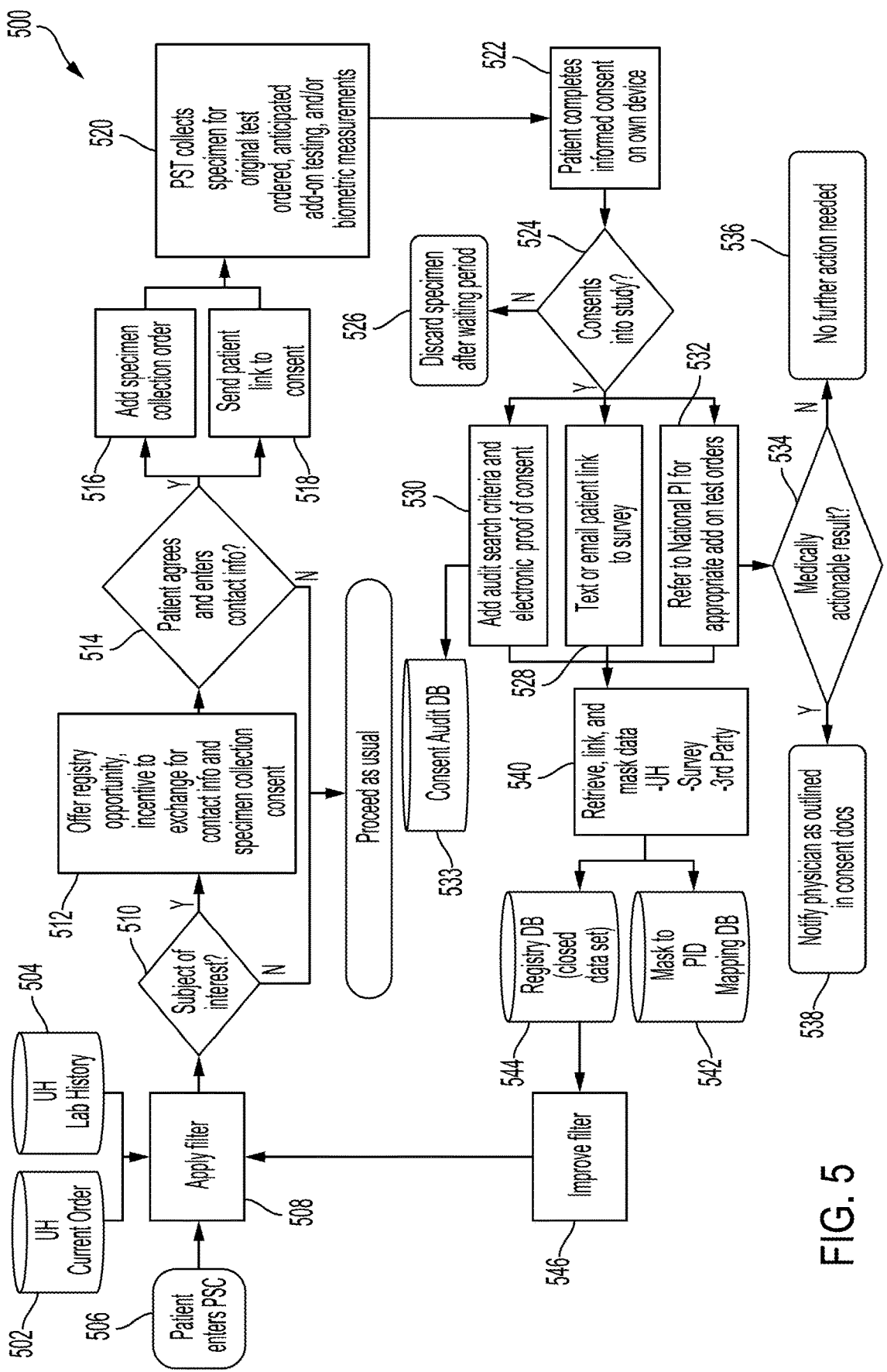
FIG. 5 shows a process of data detection according to an example.

Referring now to FIG. 5, this figure shows an example of a process 500 of disorder detection. Process 500 may be implemented using system 100 shown in FIG. 1, system 200 shown in FIG. 2, or any other suitable system according to various examples.

In block 502, a current order for a patient is obtained or received. For example, a healthcare provider can order one or more tests for a patient. As an example, and referring to FIG. 2, the current order for the patient may be received by laboratory management (LM) device(s) 225 when an order for one or more laboratory tests for a patient is ordered using one or more of the healthcare provider device(s) 210. In some examples, the laboratory tests can be ordered for a patient using a healthcare provider device and the ordered laboratory tests are received by LM device.

In some examples, in block 502, the current order for the patient can be stored in a current order database, which can be accessed by a registry management (RM) device. In block 504, laboratory history data is obtained or received. In some examples, a laboratory history database can include information from laboratory tests that have been completed. For example, the laboratory history database may include information such as laboratory tests previously ordered for patients, add-on tests for patients, and results of laboratory tests for patients. In some examples, in block 504, the LM device or the RM device can access the data stored in the laboratory history database.

In block 506, a patient visits a patient service center (PSC). In some examples, the patient can visit the PSC to have one or more specimens collected for one or more previously ordered laboratory tests (e.g. a test ordered in block 502). In some examples, in block 506, patient information can be received or obtained when the patient visits the PSC to have one or more specimens collected for one or more previously ordered laboratory tests. For example, a patient, patient service center personnel, physician, nurse practitioner, registered nurse, and/or other healthcare personnel may use one or more devices to obtain or receive the patient's name, address, phone number, email, medications, medical conditions, and/or other patient information.

In block 508, a filter is applied to the data indicating the current order (e.g., data obtained in block 502), laboratory history data (e.g., data obtained in block 504), and patient information obtained when the patient visits the PSC (e.g., data obtained in block 506). In some examples, applying a filter to the data can include analyzing the current order data, the laboratory history data, and/or the patient's information to determine whether the patient satisfies a criteria to be a subject of interest for a disorder. In some examples, in block 508, partner data (such as insurance claims, electronic health records, pharmacy data) corresponding to the patient may also be used to determine whether the patient satisfies a criteria to be a subject of interest for a disorder.

In block 510, a determination is made as to whether the patient is a subject of interest for a disorder. For example, a RM device may determine whether the patient is a subject of interest for one or more disorders. In some examples, unique criteria for each of multiple disorders is used to evaluate whether the patient is a subject of interest for any of the disorders. In another example, a laboratory profile for the disorder can be used to evaluate whether the patient is a subject of interest for any of the disorders. The patient's currently ordered laboratory tests, laboratory order test history, laboratory order test results history, and/or partner data may be accessed and used in determining whether a patient is a subject of interest for a particular disorder. RM devices may access data corresponding to the patient stored in a current orders database, laboratory history database, or partner data database to determine whether a patient is a subject of interest for a particular disorder.

In block 512, registration, an incentive, consent, or a combination of these is offered to the patient. For example, if a patient in a PSC for specimen collection for an existing laboratory testing order is determined to be a subject of interest for a disorder (e.g., in block 510), then the patient can be asked whether he or she would like to register in a disorder registry. In this example, LM device(s) and/or RM device(s) may send a registration invite to the patient via PSC device(s) and/or patient device(s). The registration invite can involve the patient agreeing to have extra specimen drawn, confirming his or her primary physician, providing consent to contact the patient's primary physician with medically relevant results, and/or consent to be contacted with medically relevant results. In some examples, the registration invite can include an incentive offered to the patient in exchange for agreeing to have extra specimen drawn, confirming his or her primary physician, providing consent to contact the patient's primary physician with medically relevant results, personal information, and/or consent to be contacted with medically relevant results.

In block 514, the patient agrees to consent and provides contact information to be registered. For example, if a patient in a PSC for specimen collection for an existing laboratory testing order is determined to be a subject of interest for a disorder (e.g., in block 510), then the patient can be asked whether he or she would like to register in a disorder registry. In this example, LM device(s) and/or RM device(s) may send a registration invite to the patient via PSC device(s) and/or patient device(s). The registration invite can involve the patient providing contact information for registering the patient in the disorder registry. In some examples, in block 514, the patient can also provide consent to have extra specimen drawn, confirm his or her primary physician, provide consent to contact the patient's primary physician with medically relevant results, and/or consent to be contacted with medically relevant results.

In block 518, the patient is sent a link to provide consent. For example, LM device(s) and/or RM device(s) may send a registration invite to the patient via PSC device(s) and/or patient device(s). The registration invite can involve the patient agreeing to have extra specimen drawn, confirming his or her primary physician, providing consent to contact the patient's primary physician with medically relevant results, and/or consent to be contacted with medically relevant results.

In block 516, a specimen collection order is added. For example, one or more orders to collect specimen for one or more laboratory tests that can indicate whether a subject has a disorder or likely has the disorder can be ordered. For example, if a patient is determined to be a subject of interest for a disorder (e.g., in block 510) and the patient registers to be included in the disorder registry (e.g., in block 514), then one or more specimen collection orders for collecting specimens required to complete add-on laboratory test(s) that indicate whether the patient has or likely has a disorder is ordered. In this example, while the patient is at the PSC, an order to collect the specimen or an order for a laboratory test that indicate whether the patient has the disorder can be ordered.

In block 520, specimen for an original laboratory test, an add-on laboratory test, and/or other biometric measurements is collected from the patient. For example, in block 520, one or more specimens for one or more laboratory tests that indicate whether a subject has a disorder or likely has the disorder is collected. For example, if a patient is determined to be a subject of interest for a disorder and the patient registers to be included in the disorder registry, then one or more add-on specimen required to complete add-on laboratory test(s) that indicate whether the patient has or likely has a disorder is determined. In this example, while the patient is at the PSC, these add-on specimen and/or other biometric measurements are collected from the patient in addition to any specimens required to complete the previously-ordered laboratory tests for the patient. Information corresponding to the add-on specimen for the add-on laboratory tests may be input into PSC device(s) and sent to LM device(s) and/or RM device(s).

In block 522, the patient provides informed consent on the patient's device. For example, one or more of devices (e.g., patient devices) can be used to provide inputs indicating that patients are interested in and consent to participating in one or more rare disease registries or studies. For example, a patient, patient service center personnel, physician, nurse practitioner, registered nurse, and/or other healthcare personnel may use one or more of devices to input that the patient is interested in and/or consents to participating in a disease study for which the patient has been determined to be a subject of interest. In some examples, a patient, patient service center personnel, physician, nurse practitioner, registered nurse, or other healthcare personnel may use one or more of devices to input that the patient consents to providing medical information about the patient.

In block 524, a determination is made as to whether the patient has consented to enrolling in the study. For example, if the patient provides a response to the enrollment interest request using the patient device corresponding to the patient that he or she is interested in enrolling in a study, then RM device(s) may determine whether the patient has consented to enrolling in the study. The patient's response to the enrollment interest request may be sent from the patient device corresponding to the patient to the RM device(s) via SMS, email, through the website, via an application or software on the patient device, or via any other suitable method.

In block 526, if the patient has not consented, then the patient's collected specimen (e.g., specimen collected in block 520) can be discarded after waiting for a suitable period of time. In block 528, a survey is sent to the patient via SMS, e-mail, or through a website or smartphone application. For example, a patient survey may be sent from RM device(s) to a patient device corresponding to the patient. In this example, the patient can complete the survey using the patient device corresponding to the patient. The completed survey can be sent from the patient device corresponding to the patient to the RM device(s).

In block 530, audit search criteria, electronic proof of consent or the combination of the two is stored. For example, if the patient provides consent, then an electronic proof of consent received by RM device(s) from patient device corresponding to the patient may be stored in a consent audit database 533 by RM device(s).

In block 532, the national principal investigator responsible for the disorder study is accessed or referenced to determine one or more add-on laboratory tests that may indicate whether the patient has a particular disorder. In some examples, in block 532, one or more algorithms or models can be accessed or used to determine one or more add-on laboratory tests that may indicate whether the patient has a particular disorder.

In block 534, a determination is made whether the one or more add-on laboratory tests (e.g., the add-on laboratory tests determined in block 532) includes an actionable result (e.g., is a laboratory test for which the patient should be tested). In block 536, no further action is taken or needed in response to determining that the one or more add-on laboratory tests is not an actionable result.

In block 538, a physician, nurse, or other healthcare provider is notified in response to determining that the one or more add-on laboratory tests is an actionable result. For example, one or more devices can be used to receive notifications regarding enrolled patients. For example, if a determination is made that the one or more add-on laboratory tests is an actionable result, then a notification can be received by one or more devices to notify the physician, nurse, or healthcare provider of the determination.

In block 540, after the survey is provided to the patient (e.g., in block 528), data is linked and can be masked. In one example, data indicating the current order (e.g., data obtained in block 502), laboratory history data (e.g., data obtained in block 504), patient information obtained when the patient visits the PSC (e.g., data obtained in block 506), data indicating whether the patient consented to enrolling in a disorder study, data indicating a specimen collected from the patient, or any other data associated with the patient can be masked. After masking the patient information, the masked patient information can be stored in a deidentified registry by RM device(s) and/or LM device(s).

In some examples, in block 542, the masked data (e.g., the data masked in block 540) can be unmasked from the deidentified registry using a hash-to-PID mapping database. In block 544, a determination can be made as to whether a registry database (e.g., a database including information about one or more patients enrolled in the registry or study) includes limited data for determining whether a patient has a disorder or likely has a disorder.

In block 546, a filter or criteria for determining whether a patient has a disorder or likely has a disorder can be refined or improved. For example, a criteria to be a subject of interest for a disorder can include one or more laboratory tests and the criteria can be automatically refined or improved to include one or more additional laboratory tests that may be designed to update or complete a laboratory profile for the disorder that indicates a likelihood of a patient having the disorder. The filter is updated with the refinements and improvements and the new filter is stored for use in future determinations. Filtering the data involves looking for specific data elements that may relate to a rare disorder. As an example, historical data may include markers such as a diagnosis code that is often mistakenly applied to rare disorder cases indicating an often-made misdiagnosis. The profile that is used for comparison purposes then indicates ranges of values for test results that may be indicative of the rare disorder. The filter and the profile include separate sets of data elements, tests, and test values for each rare disorder of interest. When patient with a rare disorder undergoes further testing, new data elements can be added or deleted from the filter in accordance with what is learned in order to update the filter. The profile can also be updated with new values or values to match date elements in the updated filter.

While some examples of devices, systems, and methods herein are described in terms of software executing on various machines, the devices, systems, and methods may also be implemented as specifically-configured hardware, such as field-programmable gate array (FPGA) specifically to execute the various methods. For example, examples can be implemented in digital electronic circuitry, or in computer hardware, firmware, software, or in a combination thereof. In one example, a device may include a processor or processors. The processor includes a computer-readable medium, such as a random access memory (RAM) coupled to the processor. The processor executes computer-executable program instructions stored in memory. Such processors may comprise a microprocessor, a digital signal processor (DSP), an application-specific integrated circuit (ASIC), field programmable gate arrays (FPGAs), and state machines. Such processors may further comprise programmable computing devices such as PLCs, programmable interrupt controllers (PICs), programmable logic devices (PLDs), programmable read-only memories (PROMs), electronically programmable read-only memories (EPROMs or EEPROMs), or other similar devices.

Such processors may include, or may be in communication with, media, for example computer-readable storage media, that may store instructions that, when executed by the processor, can cause the processor to perform the steps described herein as carried out, or assisted, by a processor. Examples of computer-readable media may include, but are not limited to, an electronic, optical, magnetic, or other storage device capable of providing a processor with computer-readable instructions. Other examples of media comprise, but are not limited to, a floppy disk, CD-ROM, magnetic disk, memory chip, ROM, RAM, ASIC, configured processor, all optical media, all magnetic tape or other magnetic media, or any other medium from which a computer processor can read. The processor, and the processing, described may be in one or more structures, and may be dispersed through one or more structures.

Examples of methods disclosed herein may be performed in the operation of computing devices. The order of the blocks presented in the examples above can be varied-for example, blocks can be re-ordered, combined, and/or broken into sub-blocks. Certain blocks or processes can be performed in parallel. Thus, while the steps of methods disclosed herein have been shown and described in a particular order, other examples may comprise the same, additional, or fewer steps. Some examples may perform the steps in a different order or in parallel. In some examples, one or more steps in a method described herein may be optional.

Reference herein to an example or implementation means that a particular feature, structure, operation, or other characteristic described in connection with the example may be included in at least one implementation of the disclosure. The disclosure is not restricted to the particular examples or implementations described as such. The appearance of the phrases "in one example," "in an example," "in one implementation," or "in an implementation," or variations of the same in various places in the specification does not necessarily refer to the same example or implementation. Any particular feature, structure, operation, or other characteristic described in this specification in relation to one example or implementation may be combined with other features, structures, operations, or other characteristics described in respect of any other example or implementation.

The foregoing description of some examples has been presented only for the purpose of illustration and description and is not intended to be exhaustive or to limit the disclosure to the precise forms disclosed. Numerous modifications and adaptations thereof will be apparent to those skilled in the art without departing from the spirit and scope of the disclosure.

That which is claimed is:

1. A system comprising:
a processing device; and
a non-transitory computer-readable medium communicatively coupled to the processing device, wherein the non-transitory computer-readable medium includes computer program code executable by the processing device to cause the processing device to perform operations comprising:
obtaining current order data, wherein the current order data indicates an order for a laboratory test for a patient;
storing patient information using a deidentified hash to mask the patient information;
applying a trained learning filter to historical data including a previous laboratory test and result for the patient, the current order data, or both, to produce filtered data including at least one mistakenly applied marker and comparing the filtered data to a profile associated with a disorder corresponding to the at least one mistakenly applied marker;
determining, in response to applying the trained learning filter, and based on patient information and the filtered data, that the patient satisfies criteria to be a subject of interest for the disorder;
determining, based on the at least one mistakenly applied marker, a first additional laboratory test for updating the profile, the trained learning filter, or both, the profile and the trained learning filter configured for automatically determining future subjects of interest for the disorder;
unmasking the patient information using a mapping database including the deidentified hash;
outputting, using the patient information and in response to the unmasking and the determining that the patient satisfies criteria to be the subject of interest for the disorder, a notification via at least one of email, short message service, or a website to a patient computing device indicating a result of the first additional laboratory test, the notification including an invitation or request for additional testing or enrollment in a study; and
retraining the trained learning filter and updating the profile using one or more new data elements determined from the first additional laboratory test to improve criteria for determining future subjects of interest for the disorder.

2. The system of claim 1, wherein determining the first additional laboratory test further comprises:
accessing a consent database to determine that the patient has consented to register in a disorder registry or has consented to enroll in a disorder study; and
determining the first additional laboratory test for indicating whether the patient has the disorder in response to determining that the patient has consented to register in the disorder registry or has consented to enroll in the disorder study.

3. The system of claim 1, wherein the operations further comprise determining, based on the result, that a second additional laboratory test for indicating whether the patient has the disorder is required.

4. The system of claim 3, wherein outputting the notification indicating the result of the first additional laboratory test comprises determining, based on the result of the first additional laboratory test, the second additional laboratory test and wherein the notification indicates the second additional laboratory test.

5. The system of claim 1, wherein the operations further comprise masking patient information, the current order data, the historical data, the first additional laboratory test, the result of the first additional laboratory test.

6. The system of claim 1, wherein the trained learning filter and the profile include separate sets of data elements, tests, and test values for each of a plurality of rare disorders.

7. The system of claim 1, wherein the operations further comprise:
outputting a survey associated with the disorder to the patient computing device; and
receiving from the patient computing device a response to the survey, wherein determining the first additional laboratory test comprises using the survey.

8. A method comprising:
obtaining current order data, wherein the current order data indicates an order for a laboratory test for a patient;
storing patient information using a deidentified hash to mask the patient information;
applying a trained learning filter to historical data including a previous laboratory test and result for the patient, the current order data, or both, to produce filtered data including at least one mistakenly applied marker and comparing the filtered data to a profile associated with a disorder corresponding to the at least one mistakenly applied marker;
determining, in response to applying the trained learning filter, and based on patient information and the filtered data, that the patient satisfies criteria to be a subject of interest for the disorder;
determining, based on the at least one mistakenly applied marker, a first additional laboratory test for updating the profile, the trained learning filter, or both, the profile and the trained learning filter configured for automatically determining future subjects of interest for the disorder;
unmasking the patient information using a mapping database including the deidentified hash;
outputting, using the patient information and in response to determining that the patient satisfies criteria to be the subject of interest for disorder, a notification via at least one of email, short message service, or a website to a patient computing device indicating a result of the first additional laboratory test, the notification including an invitation or request for additional testing or enrollment in a study; and
retraining the trained learning filter and updating the profile using one or more new data elements determined from the first additional laboratory test to improve criteria for determining future subjects of interest for the disorder.

9. The method of claim 8, wherein determining the first additional laboratory test further comprises:
accessing a consent database to determine that the patient has consented to register in a disorder registry or has consented to enroll in a disorder study; and
determining the first additional laboratory test for indicating whether the patient has the disorder in response to determining that the patient has consented to register in the disorder registry or has consented to enroll in the disorder study.

10. The method of claim 8 further comprising determining, based on the result, that a second additional laboratory test for indicating whether the patient has the disorder is required.

11. The method of claim 10, wherein outputting the notification indicating the result of the first additional laboratory test comprises determining, based on the result of the first additional laboratory test, the second additional laboratory test and wherein the notification indicates the second additional laboratory test.

12. The method of claim 8 further comprising masking patient information, the current order data, the historical data, the first additional laboratory test, or the result of the first additional laboratory test.

13. The method of claim 8, wherein the trained learning filter and the profile include separate sets of data elements, tests, and test values for each of a plurality of rare disorders.

14. The method of claim 8 further comprising:
output a survey associated with the disorder to the patient computing device; and
receive from the patient computing device a response to the survey, wherein determining the first additional laboratory test comprises using the survey.

15. A non-transitory computer-readable medium storing program code executable by a processor to cause the processor to:
obtain current order data, wherein the current order data indicates an order for a laboratory test for a patient;
store patient information using a deidentified hash to mask the patient information;
apply a trained learning filter to historical data including a previous laboratory test and result for the patient, the current order data, or both, to produce filtered data including at least one mistakenly applied marker and comparing the filtered data to a profile associated with a disorder corresponding to the at least one mistakenly applied marker;
determine, in response to applying the trained learning filter, and based on patient information and the filtered data, that the patient satisfies criteria to be a subject of interest for the disorder;
determine, based on the at least one mistakenly applied marker, a first additional laboratory test for updating the profile, the trained learning filter, or both, the profile and the trained learning filter configured for automatically determining future subjects of interest for the disorder;
unmasking the patient information using a mapping database including the deidentified hash;
output, using the patient information and in response to determining that the patient satisfies criteria to be the subject of interest for disorder, a notification via at least one of email, short message service, or a website to a patient computing device indicating a result of the first additional laboratory test, the notification including an invitation or request for additional testing or enrollment in a study; and
retrain the trained learning filter and update the profile using one or more new data elements determined from the first additional laboratory test to improve criteria for determining future subjects of interest for the disorder.

16. The non-transitory computer-readable medium of claim 15, wherein the trained learning filter and the profile include separate sets of data elements, tests, and test values for each of a plurality of rare disorders.

17. The non-transitory computer-readable medium of claim 15, wherein the program code executable to cause the processor to:
output a survey associated with the disorder to the patient computing device; and
receive from the patient computing device a response to the survey, wherein determining the first additional laboratory test comprises using the survey.

* * * * *